(12) United States Patent
Hsu et al.

(10) Patent No.: US 9,488,658 B2
(45) Date of Patent: Nov. 8, 2016

(54) BIOLOGICAL TESTING DEVICE

(71) Applicant: BIONIME CORPORATION, Taichung (TW)

(72) Inventors: Cheng-Teng Hsu, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 148 days.

(21) Appl. No.: 14/163,182

(22) Filed: Jan. 24, 2014

(65) Prior Publication Data

US 2014/0213935 A1 Jul. 31, 2014

(30) Foreign Application Priority Data

Jan. 31, 2013 (TW) .............................. 102202134 U

(51) Int. Cl.
| | |
|---|---|
| A61B 5/151 | (2006.01) |
| G01N 33/66 | (2006.01) |
| A61M 5/00 | (2006.01) |
| A61B 5/15 | (2006.01) |
| A61B 5/145 | (2006.01) |
| A61B 5/157 | (2006.01) |

(52) U.S. Cl.
CPC .............. *G01N 33/66* (2013.01); *A61B 5/1411* (2013.01); *A61B 5/14532* (2013.01); *A61B 5/15186* (2013.01); *A61B 5/150305* (2013.01); *A61M 5/003* (2013.01); *A61B 5/157* (2013.01); *A61B 5/150022* (2013.01); *A61B 5/150358* (2013.01); *A61B 2560/045* (2013.01); *A61B 2560/0418* (2013.01)

(58) Field of Classification Search
CPC . A61M 5/003; A61B 2560/04; A61B 5/157; A61B 5/150305; A61B 2560/0418; G01N 33/4875

See application file for complete search history.

(56) References Cited

U.S. PATENT DOCUMENTS

| | | | |
|---|---|---|---|
| 2005/0126938 A1* | 6/2005 | Uehata ............... | G01N 33/4875 206/305 |
| 2010/0081967 A1 | 4/2010 | Charlton | |
| 2010/0198107 A1 | 8/2010 | Groll et al. | |
| 2010/0206751 A1* | 8/2010 | Wessel ............... | A61B 5/14532 206/38 |
| 2013/0338464 A1* | 12/2013 | Stainken ............ | A61B 5/14532 600/365 |

FOREIGN PATENT DOCUMENTS

WO    2010096054    8/2010

* cited by examiner

*Primary Examiner* — Michael C Stout
*Assistant Examiner* — Nicholas E Kolderman
(74) *Attorney, Agent, or Firm* — Kirton McConkie; Evan R. Witt

(57) ABSTRACT

A biological testing device includes a housing body having a meter storage compartment, and a testing meter that is disposed in the meter storage compartment and that operates with a biosensor strip which is disposed after being used. The housing body further has a waste storage compartment that is separated from the meter storage compartment and that has a waste take-out opening, and an insertion hole for inserting the used biosensor strip into the waste storage compartment. The waste take-out opening is larger than the insertion hole. The waste take-out opening is normally closed and is openable for permitting taking out of the used biosensor strip from the waste storage compartment.

6 Claims, 22 Drawing Sheets

BIOLOGICAL TESTING DEVICE

CROSS-REFERENCE TO RELATED APPLICATION

This application claims priority of Taiwanese Application No. 102202134, filed on Jan. 31, 2013, the disclosure of which is incorporated herein by reference.

BACKGROUND OF THE INVENTION

1. Field of the Invention

The invention relates to a testing device, more particularly to a biological testing device for testing a sample of body liquid.

2. Description of the Related Art

A conventional glucose testing system (for example, U.S. Patent Publication No. 20100081967) or a blood glucose meter having a lancing device (for example, U.S. Patent Publication No. 20100198107) can permit a user to obtain blood sample and then conduct blood glucose testing and analysis. The used bio sensor strip or lancet is, in fact, an infectious medical waste. According to the medical regulatory requirements, the medical waste (s) should be disposed in an appropriate recycling site or collected in a bottle to ensure environmental health and safety. However, the aforesaid prior art is not designed with a storage compartment for permitting a user to safely store the used biosensor strip or lancet, so that use of the aforesaid prior art is inconvenient. Although a storage area is disclosed in U.S. Patent Publication No. 20100081967, it is not designed to store used biosensor strips or lancets.

SUMMARY OF THE INVENTION

Therefore, the object of the present invention is to provide a biological testing device that can permit temporary and safe storage of used biosensor strips and/or lancets.

According to this invention, a biological testing device for testing a sample comprises a housing body having a meter storage compartment, and a testing meter that is disposed in the meter storage compartment and that operates with a biosensor strip which is disposed after being used. The housing body further has a waste storage compartment that is separated from the meter storage compartment and that has s a waste take-out opening, and an insertion hole communicated with the waste storage compartment for inserting the used biosensor strip into the waste storage compartment. The waste take-out opening is larger than the insertion hole. The insertion hole is separated from the waste take-out opening and has a narrow oblong shape substantially similar to a cross section of the used biosensor strip. The waste take-out opening is normally closed and is openable for permitting taking out of the used biosensor strip from the waste storage compartment.

The efficiency of this invention resides in that it can permit a user to insert the used biosensor strip or lancet into the waste storage compartment via the insertion hole, so that the used biosensor strip or lancet can be conveniently, safely, and temporarily stored in the waste storage compartment.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
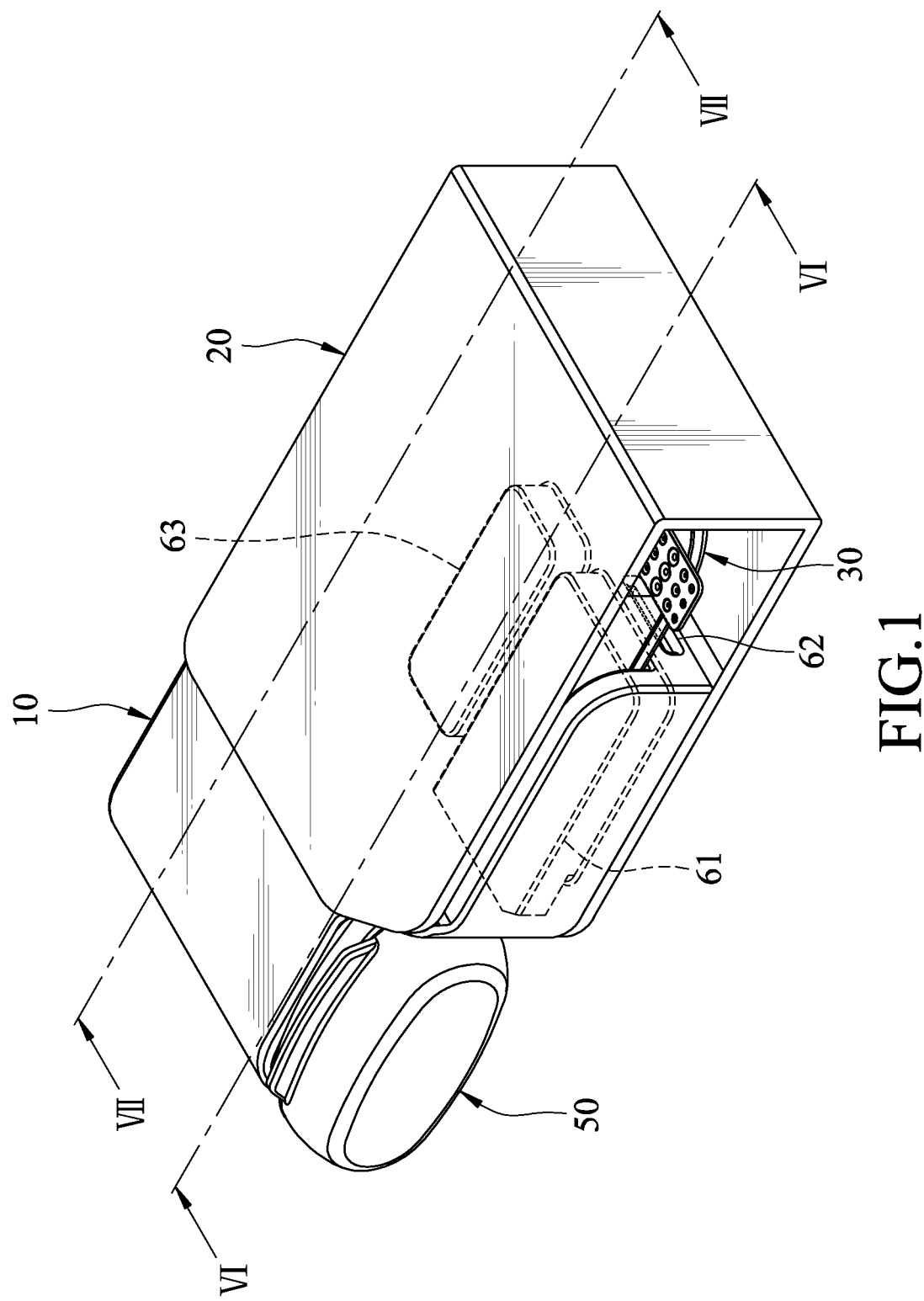
FIG. 1 is a perspective view of a biological testing device according to the first preferred embodiment of this invention.

Before the present invention is described in greater detail, it should be noted that like elements are denoted by the same reference numerals throughout the disclosure.

Referring to FIGS. 1 to 11, a biological testing device according to the first preferred embodiment of the present invention is suitable for testing a liquid sample (for example, blood), and is shown to comprise a housing body 10, a cover 20, a testing meter 30, a lancing pen 40 and a biosensor strip container 50.

Figure 3:
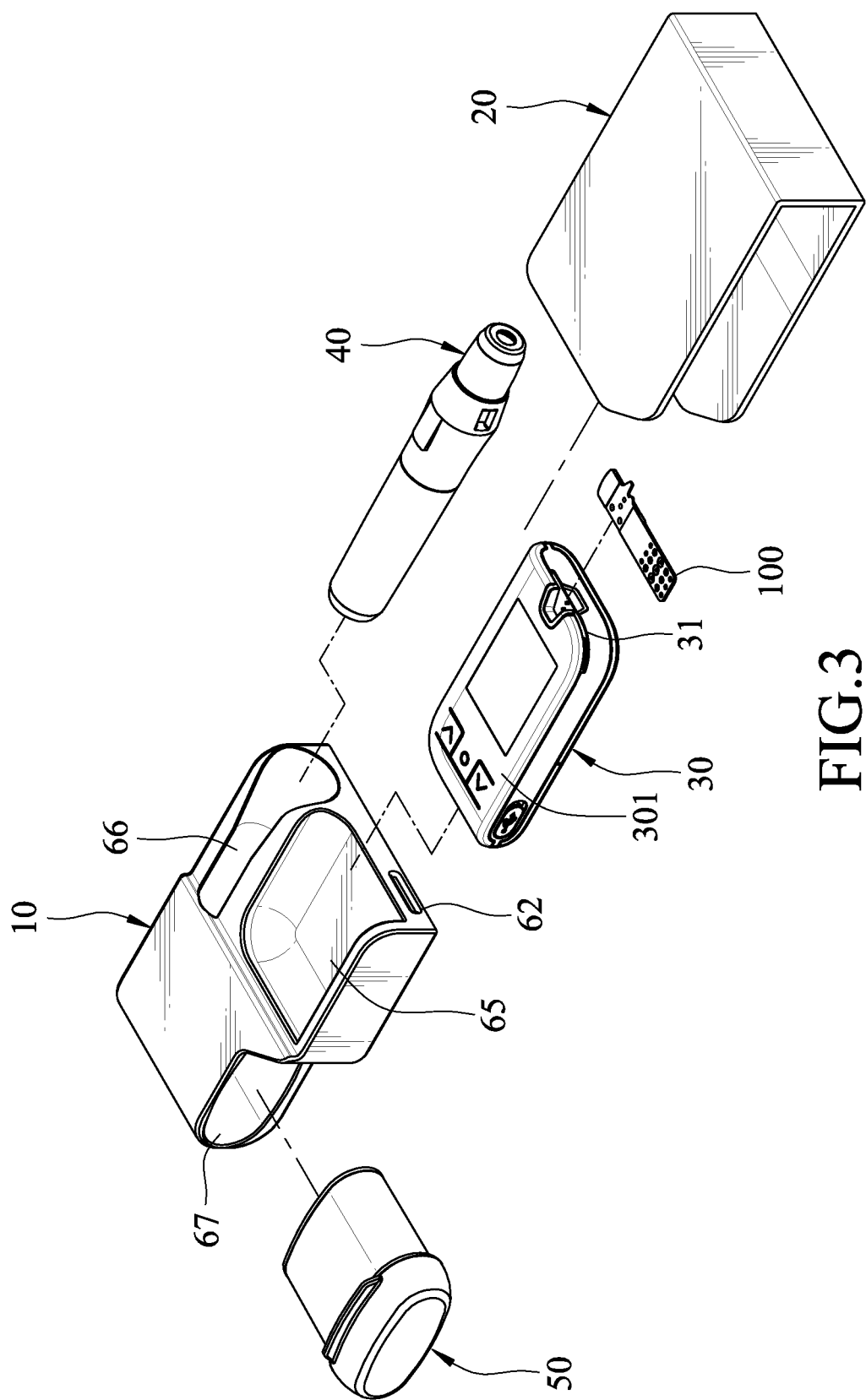
FIG. 3 is an exploded perspective view of the first preferred embodiment.
Figure 4:
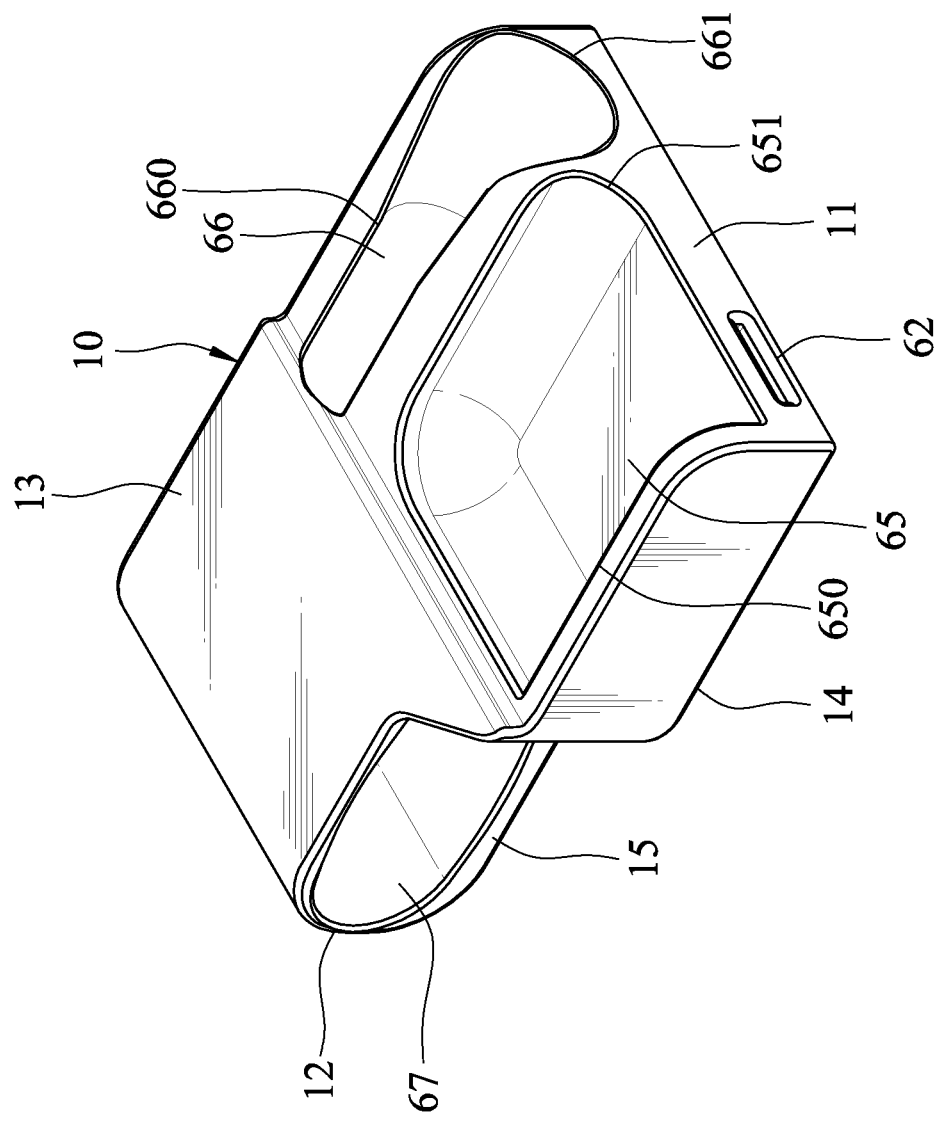
FIG. 4 is a perspective view of a housing body of the first preferred embodiment.
Figure 5:
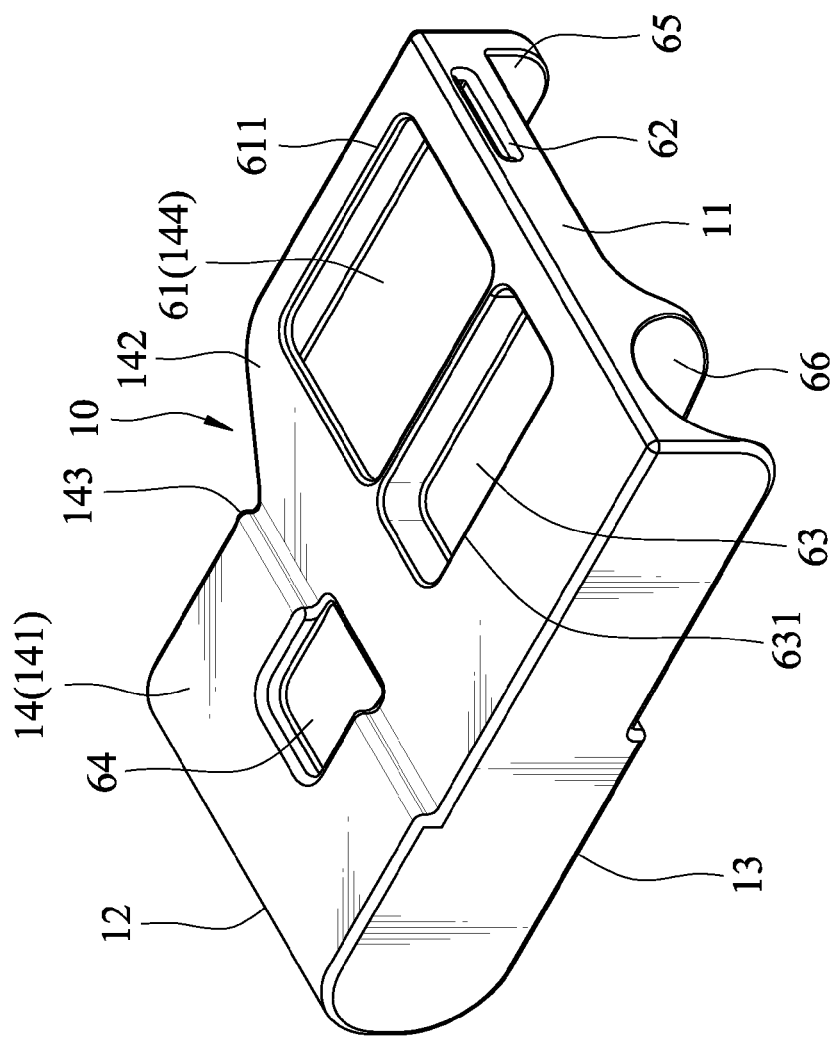
FIG. 5 is a bottom perspective view of the housing body of the first preferred embodiment.

With reference to FIGS. 3 to 5, the housing body 10 has a front end 11, a rear end 12, a top surface 13, a bottom surface 14 and a side surface 15. The housing body 10 further has a waste storage compartment 61 with a waste take-out opening 611, an insertion hole 62 formed in the front end 11 and communicated with the waste storage compartment 61, a spare compartment 63 that is adjacent to the waste storage compartment 61 and that has a spare take-out opening 631 formed in the bottom surface 14, an operating groove 64 extending inwardly from the bottom surface 14, a meter storage compartment 65 separated from the waste storage compartment 61, a pen storage compartment 66 adjacent to the meter storage compartment 65, and a container storage compartment 67 that is formed in proximity to the rear end 12 and that opens at the side surface 15. In this embodiment, the meter storage compartment 65 has a top opening 650 at the top surface 13, and a flared front opening 651 at the front end 11 for guiding entrance of the testing meter 30 into the meter storage compartment 65. The pen storage compartment 66 also has a top opening 660 at the top surface 13, and a flared front opening 661 at the front end 11 for guiding entrance of the lancing pen 40 into the pen storage compartment 66. Further, the waste take-out opening 611 is formed in the bottom surface 14, is normally closed, and is larger than the insertion hole 62. The insertion hole 62 is separated from the waste take-out opening 611, and has a narrow oblong shape substantially similar to a cross section of a biosensor strip 100. In an alternative embodiment, the insertion hole 62 may be disposed on the side surface 15 of the housing body 10.

Figure 6:
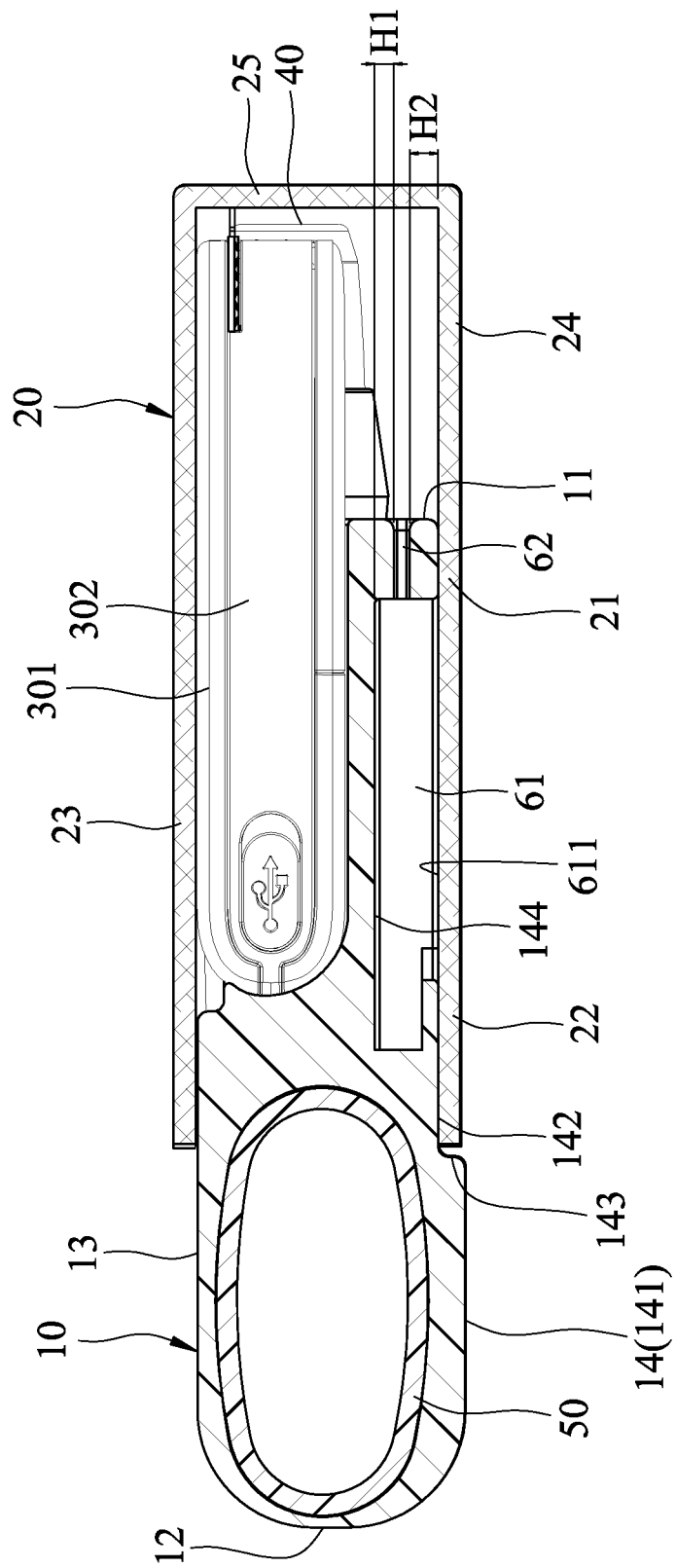
FIG. 6 is an assembled sectional view of the first preferred embodiment taken along line VI-VI of FIG. 1.
Figure 7:
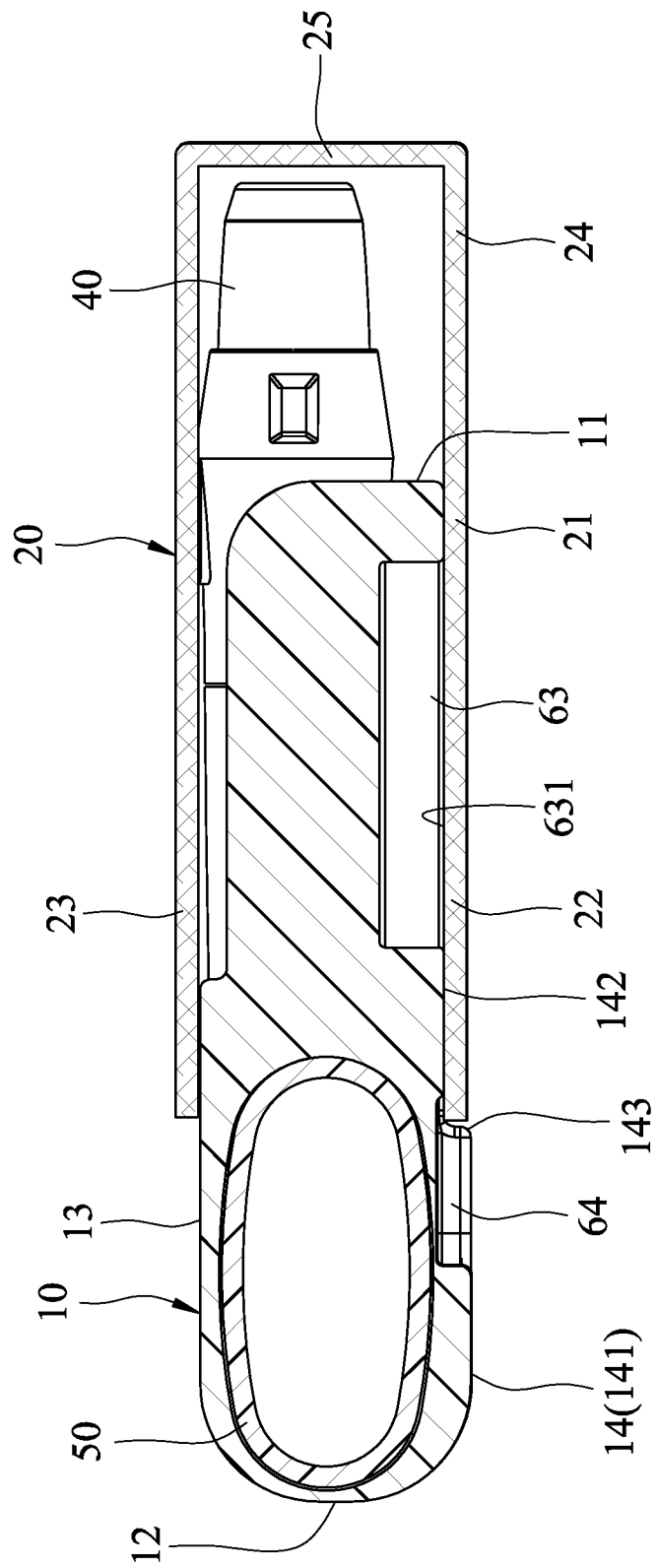
FIG. 7 is an assembled sectional view of the first preferred embodiment taken along line VII-VII of FIG. 1.

With reference to FIGS. 5 to 7, the bottom surface 14 of the housing body 10 has a non-indented portion 141 proximate to the rear end 12, an indented portion 142 proximate to the front end 11, and a shoulder 143 formed between the non-indented and indented portions 141, 142. In this embodiment, the waste take-out opening 611 and the spare take-out opening 631 are formed in the indented portion 142. The operating groove 64 is formed in the non-indented portion 141 and has a front end extending through the shoulder 143 into the indented portion 142. The housing body 10 further has s a separation wall 144 that separates the meter storage compartment 65 and the waste storage compartment 61. The separation wall 144 is spaced apart from the insertion hole 62 by a first distance (H1) (see FIG. 6).

The testing member 30 has a meter casing 301, and a meter body 302 (see FIG. 6) received in the meter casing 301.

Figure 2:
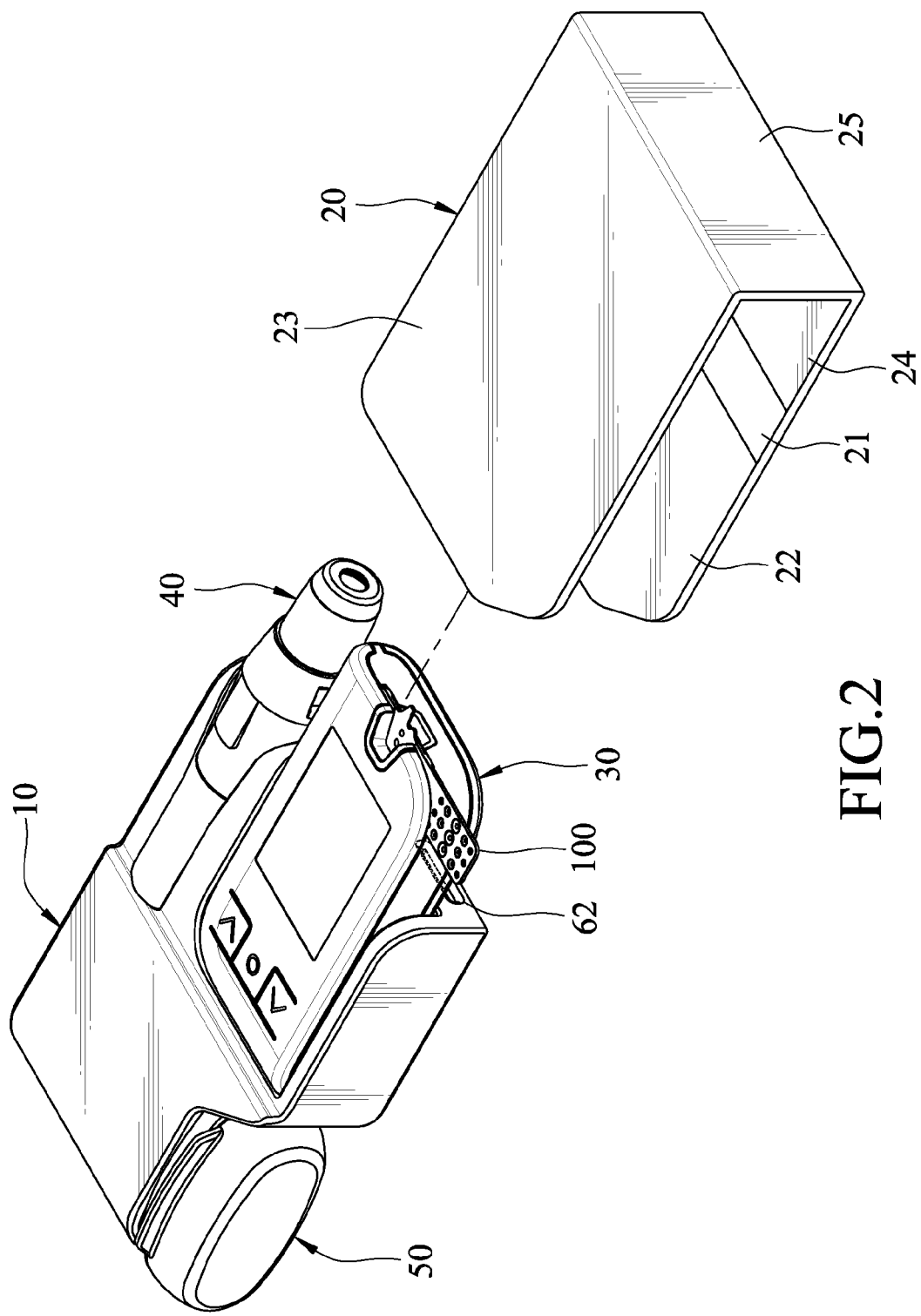
FIG. 2 is a partial exploded perspective view of the first preferred embodiment.

As shown in FIGS. 2, 6 and 7, the cover 20 has a positioning section 21 positioned on the indented portion 142, a first cover section 22 that extends rearwardly from and that is pivotable relative to the positioning section 21, a first pivot section 24 that extends forwardly from and that is pivotable relative to the positioning section 21, a second pivot section 25 that extends upwardly from and that is pivotable relative to the first pivot section 24, and a second cover section 23 that extends rearwardly from and that is pivotable relative to the second pivot section 25. In this embodiment, the cover 20 is a leather cover. Alternatively, the cover 20 may be made of other pivotable material, such as rubber, silicone, etc. Further, the first cover section 22 may be made of a blood stain resistant material or other material that is easy to clean. Moreover, the cover 20 may also be detached from the housing body 10 so as to facilitate its cleaning.

Referring once again to FIGS. 6 and 7, the first cover section 22 is selectively positioned on the indented portion 142 so as to openably close the waste take-out opening 611, the spare take-out opening 631 and a portion of the operating groove 64. When the first cover section 22 is positioned on the indented portion 142, an inner side of the first cover section 22 is spaced apart from the insertion hole 62 by a second distance (H2). In this embodiment, a magnetic component (not shown) may be disposed on the indented portion 142 at a predetermined position, and an interior of the first cover section 22 may be provided with a magnetically attractive material (not shown) corresponding to the magnetic component, so that the first cover section 22 can be magnetically attached to or detached from the indented portion 142. When the first cover section 22 is magnetically attached to the indented portion 142, the first cover section 22 closes the waste and spare take-out openings 611, 631. When the first cover section 22 is pulled open through the operating groove 64 so as to detach from the indented portion 142, the waste and spare take-out openings 611, 631 are open.

The second cover section 23 is selectively positioned on the top surface 13 so as to openably cover the testing meter 30 and the lancing pen 40. In this embodiment, a magnetic component (not shown) may be disposed on the top surface 13 at a predetermined position, and an interior of the second cover section 23 may be provided with a magnetically attractive material (not shown) corresponding to the magnetic component, so that the second cover section 23 can be magnetically attached to or detached from the top surface 13 of the housing body 10. When the second cover section 23 is magnetically attached to the top surface 13, the second cover section 23 closes the top openings 650, 660 of the meter storage compartment 65 and the pen storage compartment 66. When the second cover section 23 is detached from the top surface 13, the top openings 650, 660 of the meter storage compartment 65 and the pen storage compartment 66 are open to reveal the testing meter 30 and the lancing pen 40. Further, when the second cover section 23 is magnetically attached to or detached from the top surface 13, the second pivot section 25 cooperates with the second cover section 23 so as to selectively cover and uncover the insertion hole 62 and the front openings 651, 661 of the meter storage compartment 65 and the pen storage compartment 66. A front end of the testing meter 30 and a front end of the lancing pen 40 are respectively exposed from the front openings 651, 661 when the second cover section 23 is detached from the top surface 13.

It should be noted that the aforesaid magnetic attraction positioning is only one of the feasible implementations of the present invention, other method which can selectively position the first and second cover sections 22, 23 on the housing body 10 may also be employed.

With reference to FIGS. 2 and 3, in this embodiment, the testing meter 30 is removably disposed in the meter storage compartment 65, the lancing pen 40 is removably disposed in the pen storage compartment 66, and the biosensor strip container 50 is removably disposed in the container storage compartment 67. Further, the testing meter 30 is a blood glucose meter. The testing meter 30 operates with a biosensor strip 100, and has an insertion groove 31 for insertion of the biosensor strip 100 therein. The lancing pen 40 includes a lancet (not shown) for obtaining a blood sample. The biosensor strip container 50 is used for storing new or unused biosensor strips 100. Because the biosensor strip container 50 has a substantially oval shape, the entire appearance of this invention is slim and light, so that the present invention can be easily carried by a user.

Figure 8:
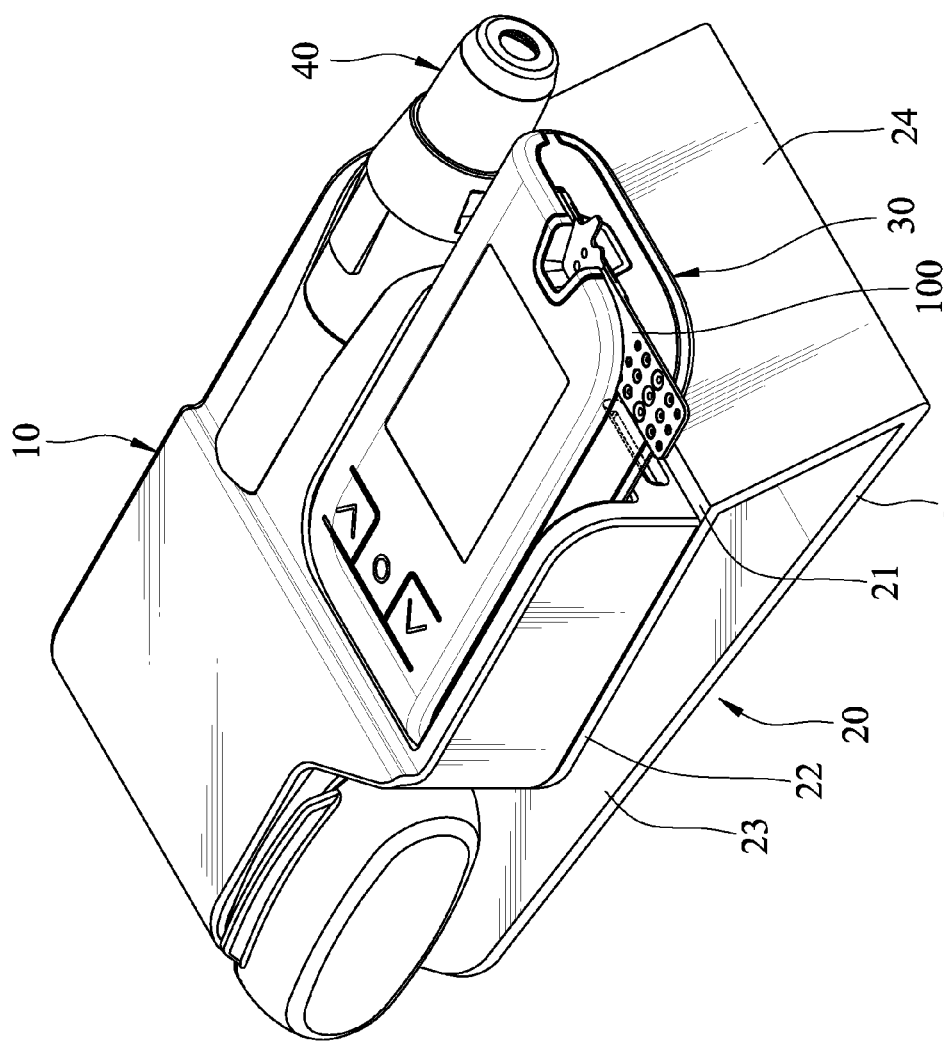
FIG. 8 is a perspective view of the first preferred embodiment in a state of use.
Figure 9:
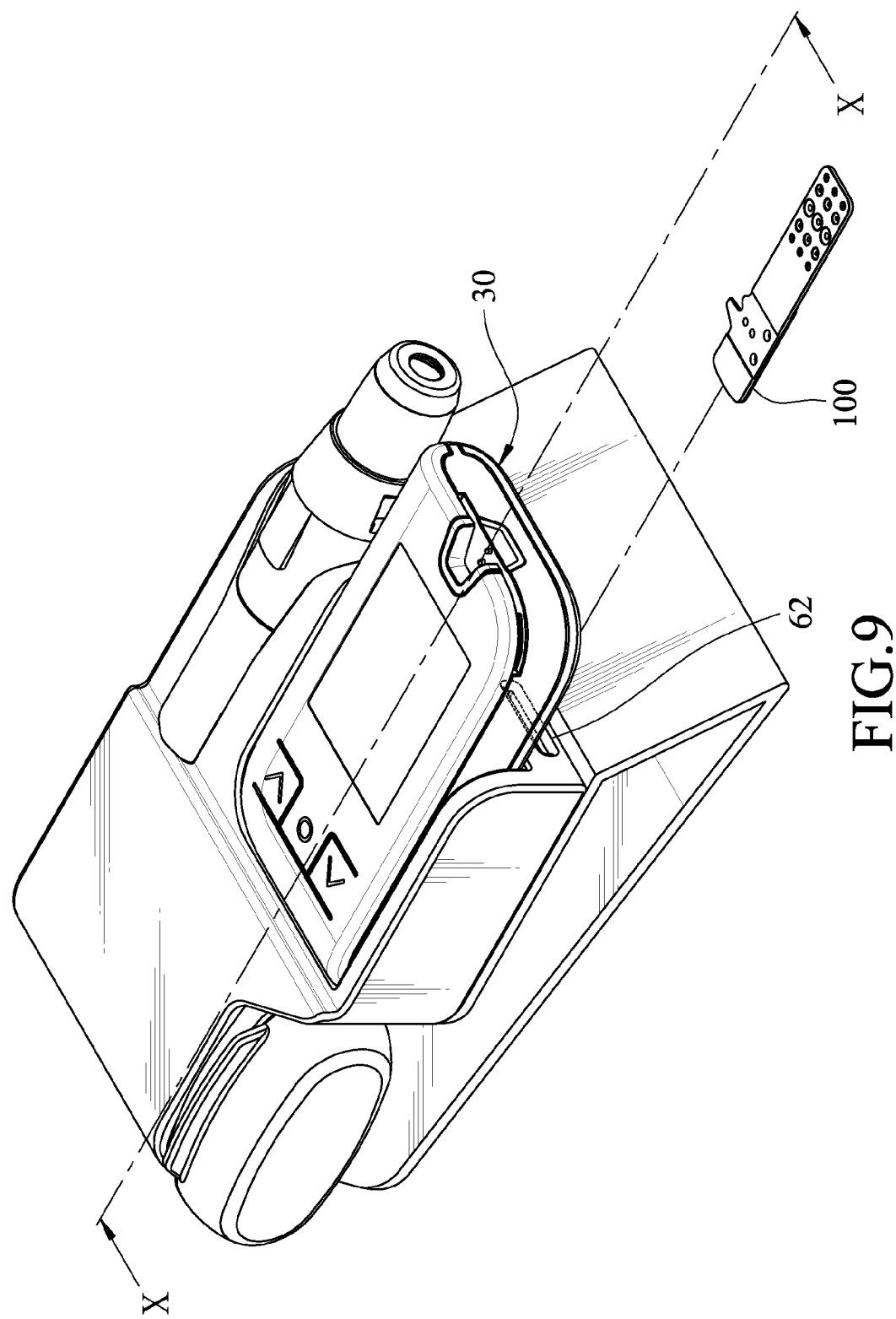
FIG. 9 is a view similar to FIG. 8, but illustrating how a used biosensor strip is removed from a testing meter and is then inserted into an insertion hole.
Figure 10:
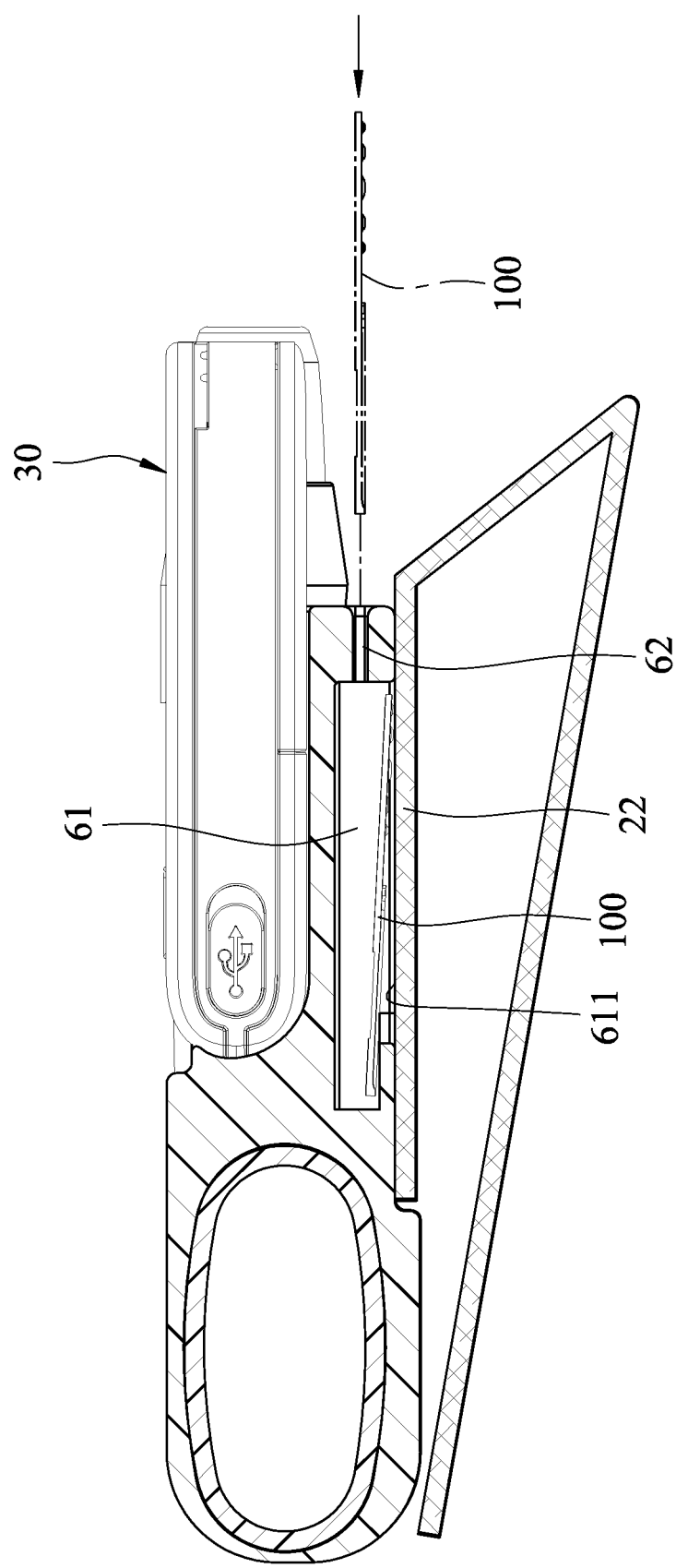
FIG. 10 is a sectional view of the first preferred embodiment taken along line X-X of FIG. 9.
Figure 11:
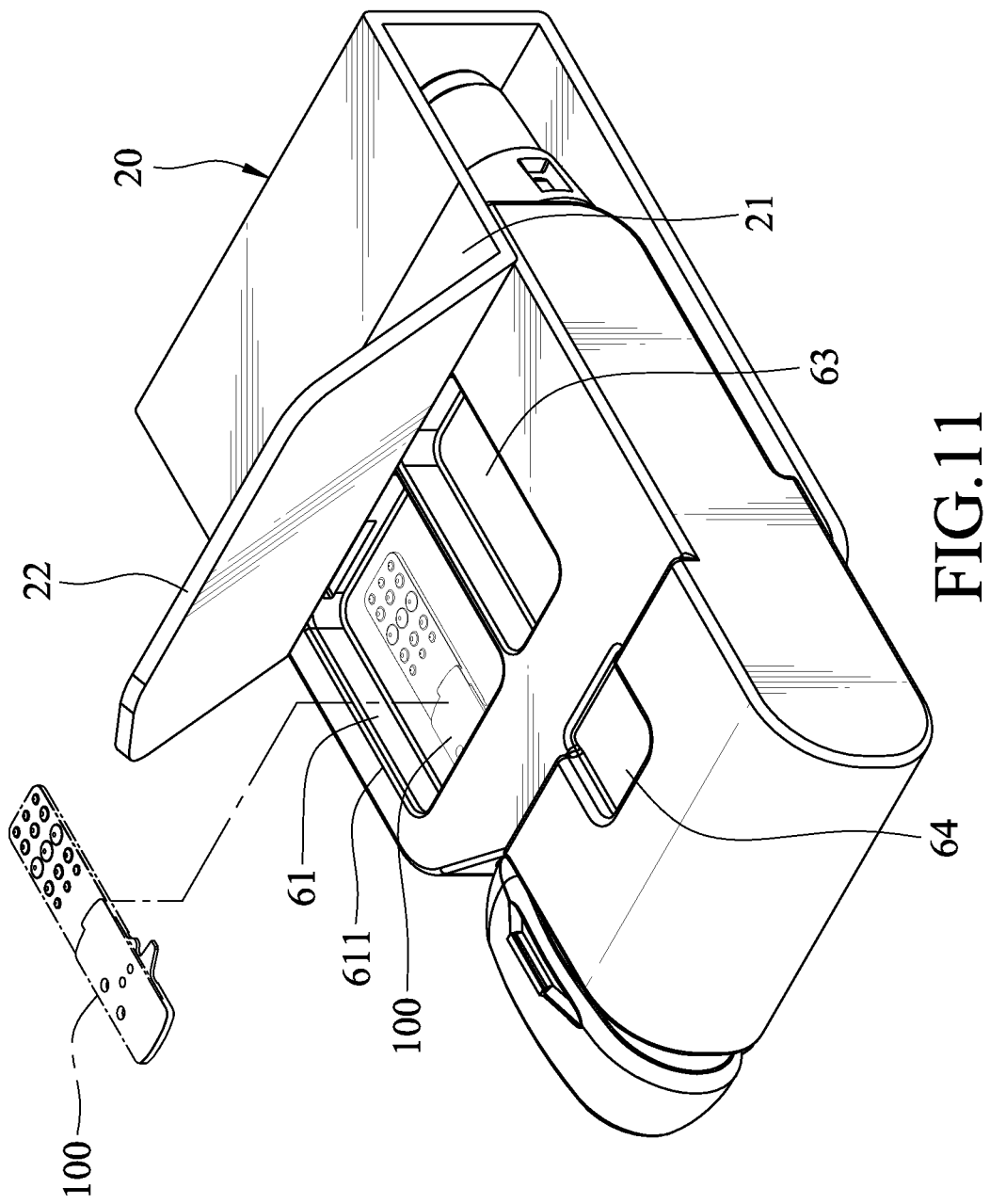
FIG. 11 is a bottom perspective view of FIG. 1, illustrating how the used biosensor strip can be taken out from a waste storage compartment.

With reference to FIG. 8, when the user desires to measure his/her blood sugar, the second cover section 23 is detached from the top surface 13 and is folded over the bottom surface 14. Without removing the testing meter 30 and the lancing pen 40 from the housing body 10, the lancet (not shown) is pushed out from the lancing pen 40 to prick a finger of the user so as to obtain a blood sample (not shown). A drop of blood from the user's finger is dripped onto a biosensor strip 100, after which the biosensor strip 100 is inserted into the insertion groove 31 of the testing meter 30. The testing meter 30 then measures the blood sugar concentration of the user's blood through the blood sample on the biosensor strip 100. Next, with reference to FIGS. 9 and 10, after testing, the used biosensor strip 100 is pulled and removed from the testing meter 100, and is inserted into the insertion hole 62 so as to be received in the waste storage compartment 61 for temporary storage. At this time, the waste take-out opening 611 is closed by the first cover section 22 to ensure the safe storage of the used biosensor strip 100 in the waste storage compartment 61. Afterwards, with reference to FIG. 11, when the user arrives an appropriate recycling site or has a collection bottle, the first cover section 22 is pivoted forwardly relative to the positioning section 21 to open or reveal the waste take-out opening 611, thereby facilitating removal of the used biosensor strip 100 from the waste storage compartment 61 for discard. Further, the used lancet may also be temporarily stored in the waste storage compartment 61.

It is worth mentioning that spare lancets or spare materials, such as alcohol swabs, may be stored in the spare compartment 63 and may be removed from the same by opening the first cover section 22.

From the aforesaid description, the advantages of the present invention may be summarized as follows:

1. The housing body 10 of this invention is provided with the waste storage compartment 61 and the insertion hole 62 to facilitate temporary storage of the used biosensor strip 100 by inserting the used biosensor strip 100 into the waste storage compartment 61 via the insertion hole 62. Further, the present invention uses the first cover section 22 of the cover 20 to timely open or close the waste take-out opening 611 of the waste storage compartment 61 so that safe storage of the used biosensor strip 100 in the waste storage compartment 61 can be ensured. Compared to the prior art, the present invention not only can permit easy and quick performance of blood testing, but also can conform to the safety and health requirements during use thereof.

2. Because the insertion hole 62 is spaced apart from the separation wall 144 by the first distance (H1) (see FIG. 6) and is spaced apart from the inner side of the first cover section 22 by the second distance (H2) (see FIG. 6), the used biosensor strip 100 can be effectively prevented from falling out of the waste storage compartment 61 via the insertion hole 62.

3. The housing body 10 of this invention is further provided with the spare compartment 63 that can be timely opened or closed to facilitate storage of spare materials (for example, spare lancets, alcohol swabs, etc.) according to the use requirement.

Figure 12:
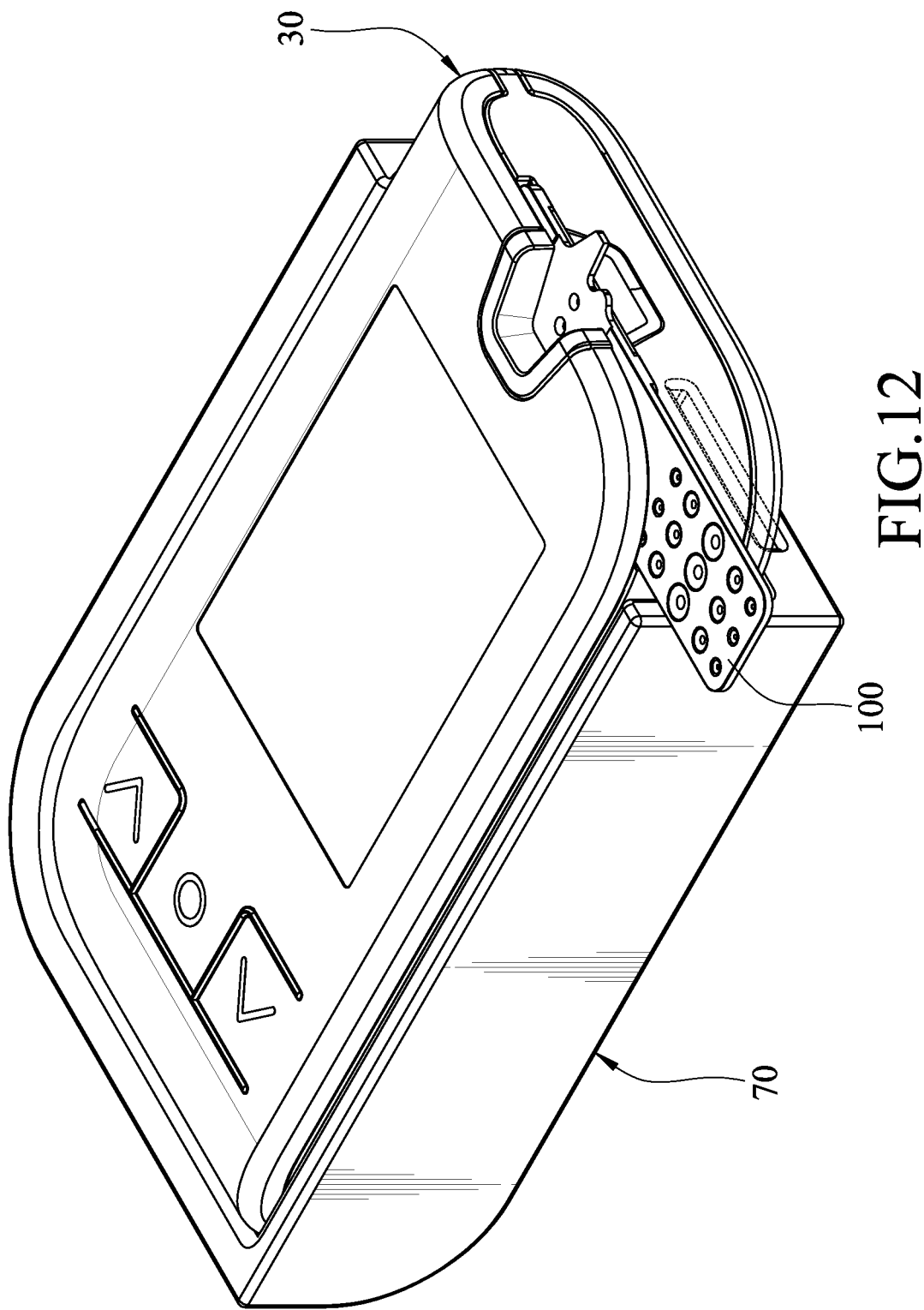
FIG. 12 is a perspective view of a biological testing device according to the second preferred embodiment of this invention.
Figure 13:
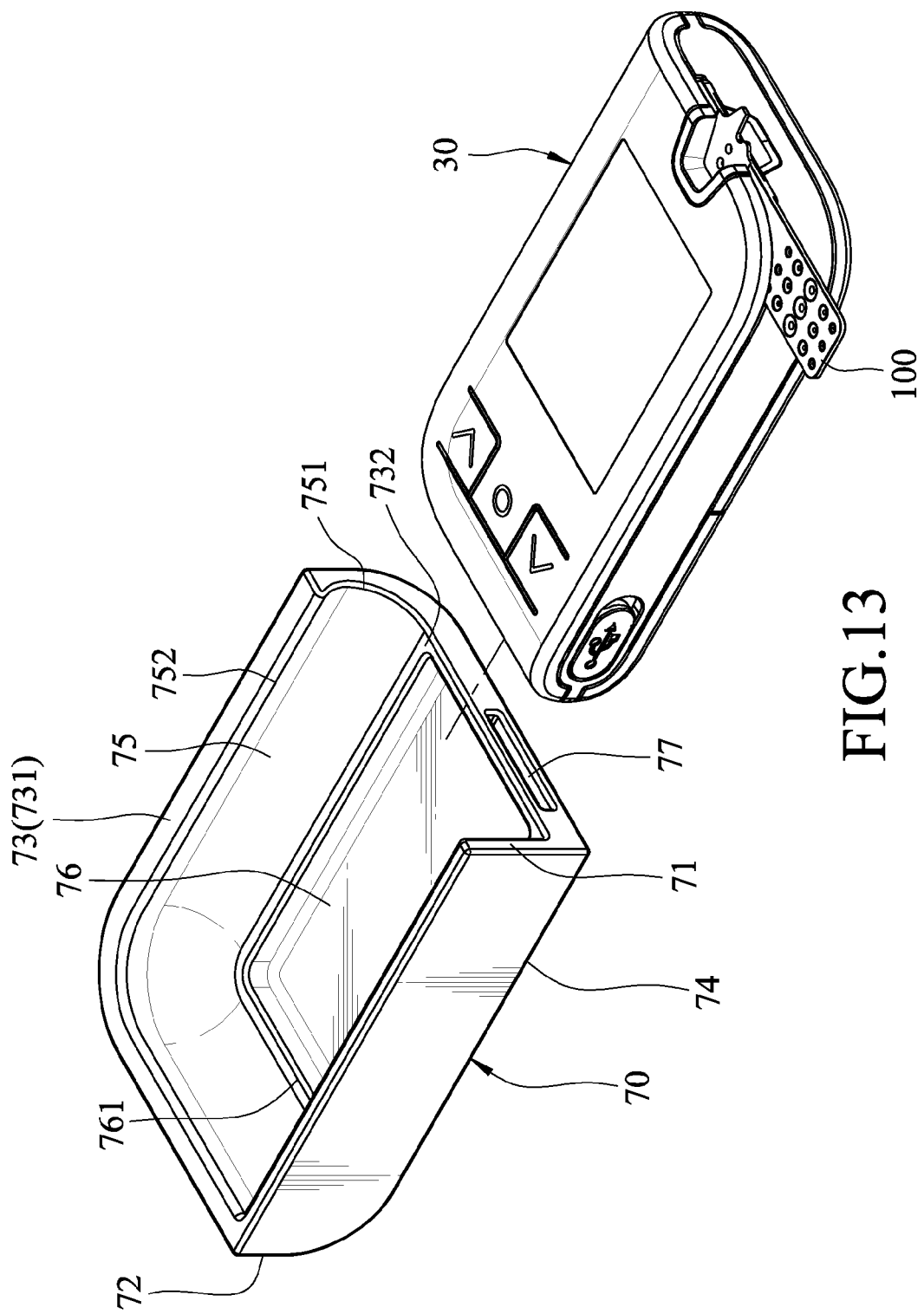
FIG. 13 is an exploded perspective view of the second preferred embodiment.
Figure 14:
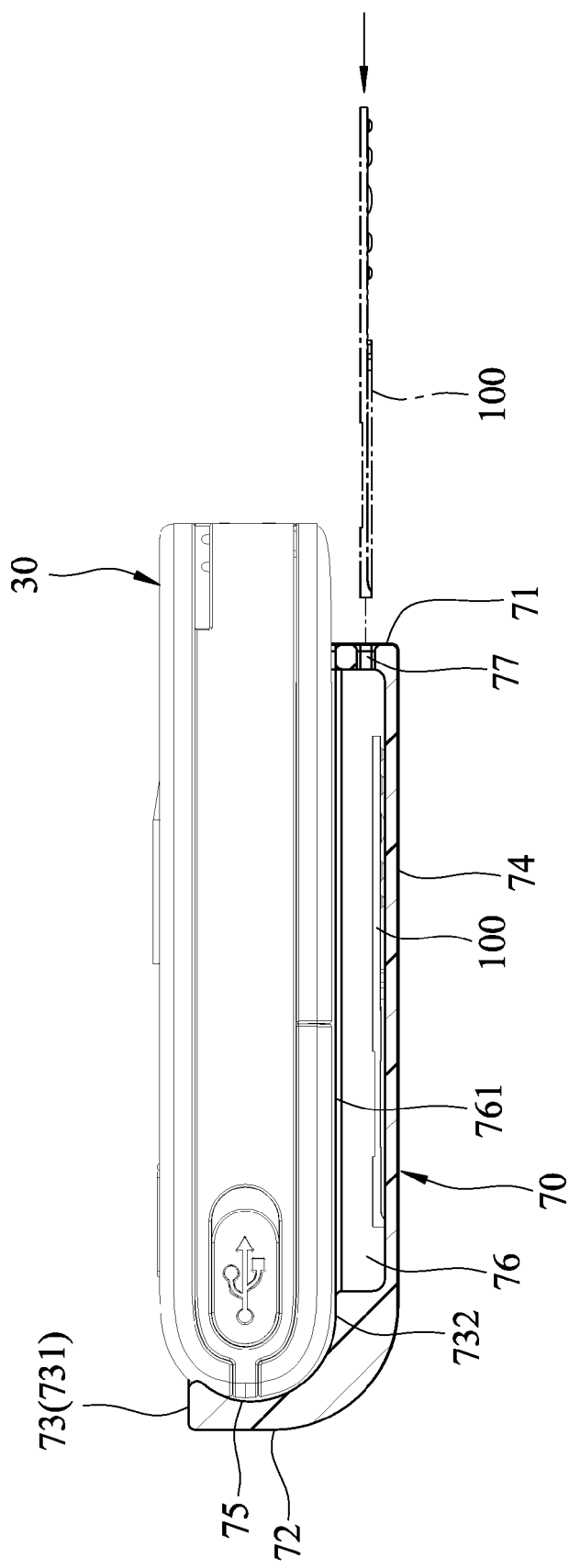
FIG. 14 is an assembled sectional view of the second preferred embodiment, illustrating how a used biosensor strip is inserted into a waste storage compartment via an insertion hole.

Referring to FIGS. 12 to 14, the second preferred embodiment of the biological testing device according to the present invention is shown to be similar to the first preferred embodiment. Particularly, the housing body 70 has a front end 71, a rear end 72, a top surface 73, a bottom surface 74, a meter storage compartment 75, a waste storage compartment 76, an insertion hole 77 communicating with the waste storage compartment 76, and a separation wall 732 separating the meter storage compartment 75 and the waste storage compartment 76. However, in this embodiment, the housing body 70 is a back clamp, and is not provided with a pen storage compartment. It is understandable that the housing body 70 may also be provided with a spare compartment (not shown) at an appropriate position.

The meter storage compartment 75 has a front opening 751 at the front end 71, and a top opening 752 at the top surface 73.

The waste storage compartment 76 has a waste take-out opening 761 formed in the separation wall 732 to communicate the waste storage compartment 76 with the meter storage compartment 75.

The insertion hole 77 is formed in the front end 71, and is disposed below the front opening 751.

The testing meter 30 is removably disposed in the meter storage compartment 75 to openably close the waste take-out opening 761 of the waste storage compartment 76. In this embodiment, the testing meter 30 is a blood glucose meter that operates with a biosensor strip 100.

After testing, the biosensor strip 100 is pulled and removed from the testing meter 30, and is inserted into the insertion hole 77 so as to be received in the waste storage compartment 76 for temporary storage. At this time, the waste take-out opening 761 is covered by a bottom side of the testing meter 30 to ensure safe storage of the used biosensor strip 100 in the waste storage compartment 76. It is understandable that when the testing meter 30 is moved out from the meter storage compartment 75, the used biosensor strip 100 can be removed from the waste storage compartment 76 for discard.

The advantages described in the first preferred embodiment can be similarly achieved using the second preferred embodiment.

Figure 15:
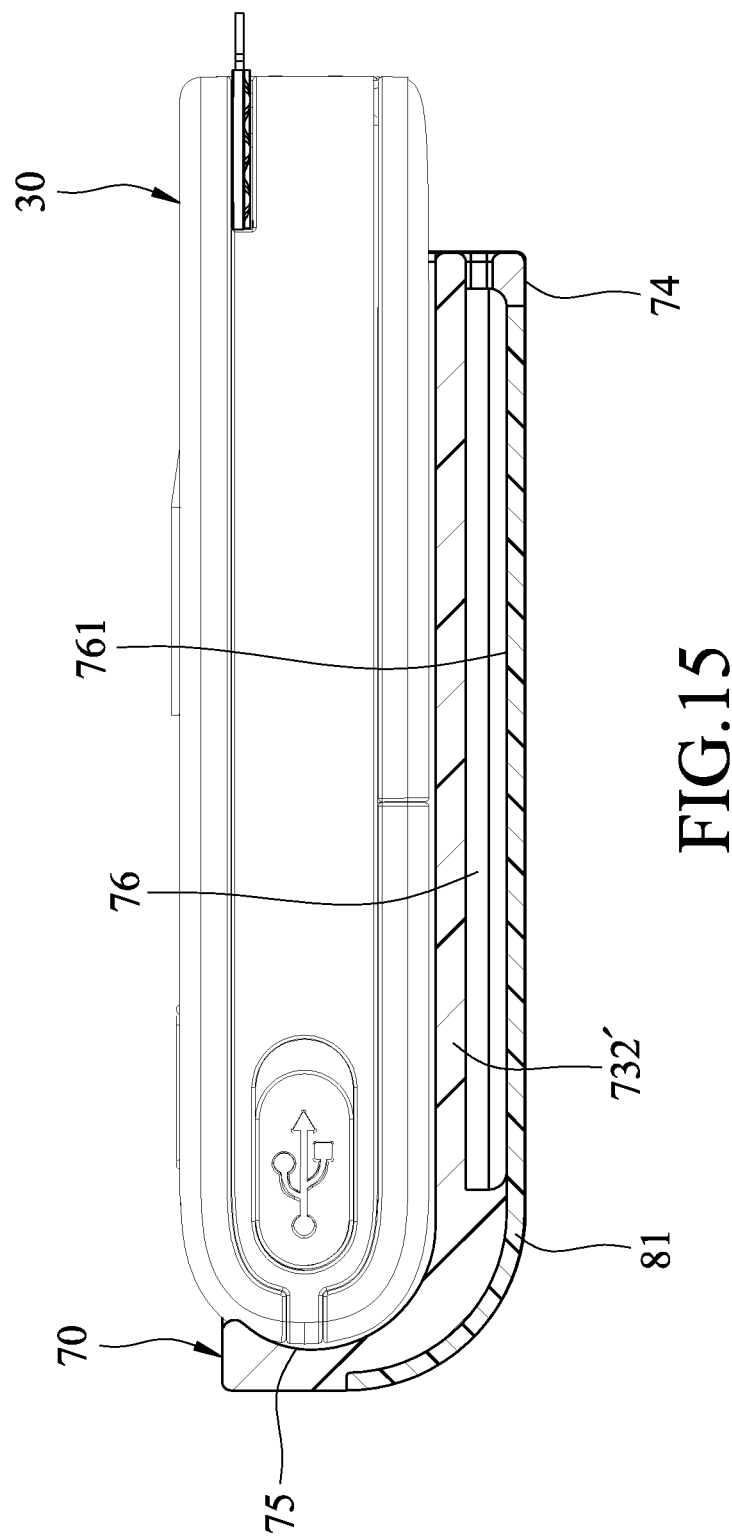
FIG. 15 is an assembled sectional view of a biological testing device according to the third preferred embodiment.

Referring to FIG. 15, the third preferred embodiment of the biological testing device according to the present invention is shown to be similar to the second preferred embodiment. However, in this embodiment, the waste take-out opening 761 of the waste storage compartment 76 is formed in the bottom surface 74 of the housing body 70. The separation wall 732' separates the meter storage compartment 75 and the waste storage compartment 76.

A bottom cover 81 is removably disposed on the bottom surface 74 to openably close the waste take-out opening 761.

The advantages described in the first preferred embodiment can be similarly achieved using the third preferred embodiment.

Figure 16:
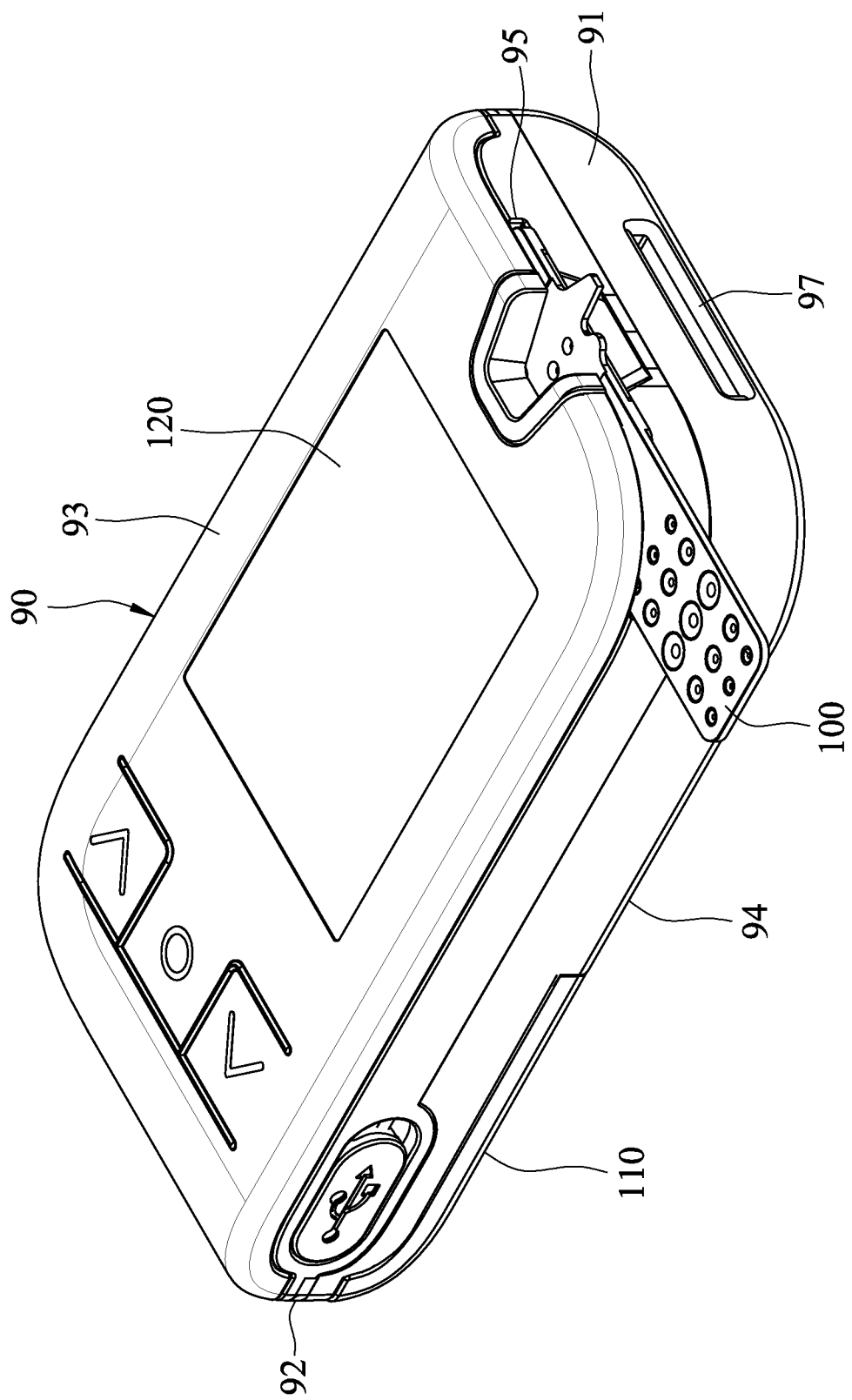
FIG. 16 is a perspective view of a biological testing device according to the fourth preferred embodiment of this invention.
Figure 17:
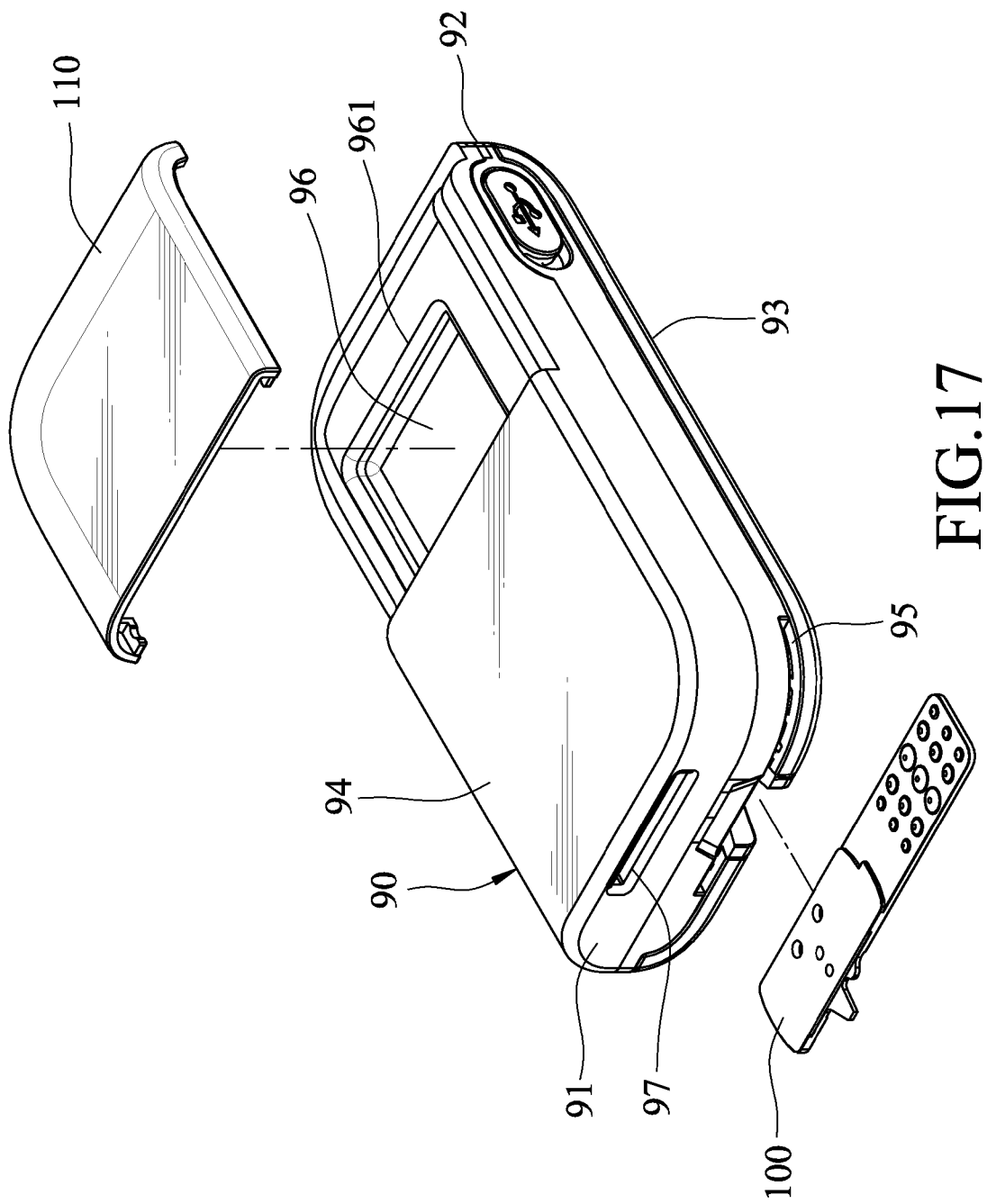
FIG. 17 is a bottom perspective view of the fourth preferred embodiment, illustrating a bottom cover being removed to expose a waste storage compartment.
Figure 18:
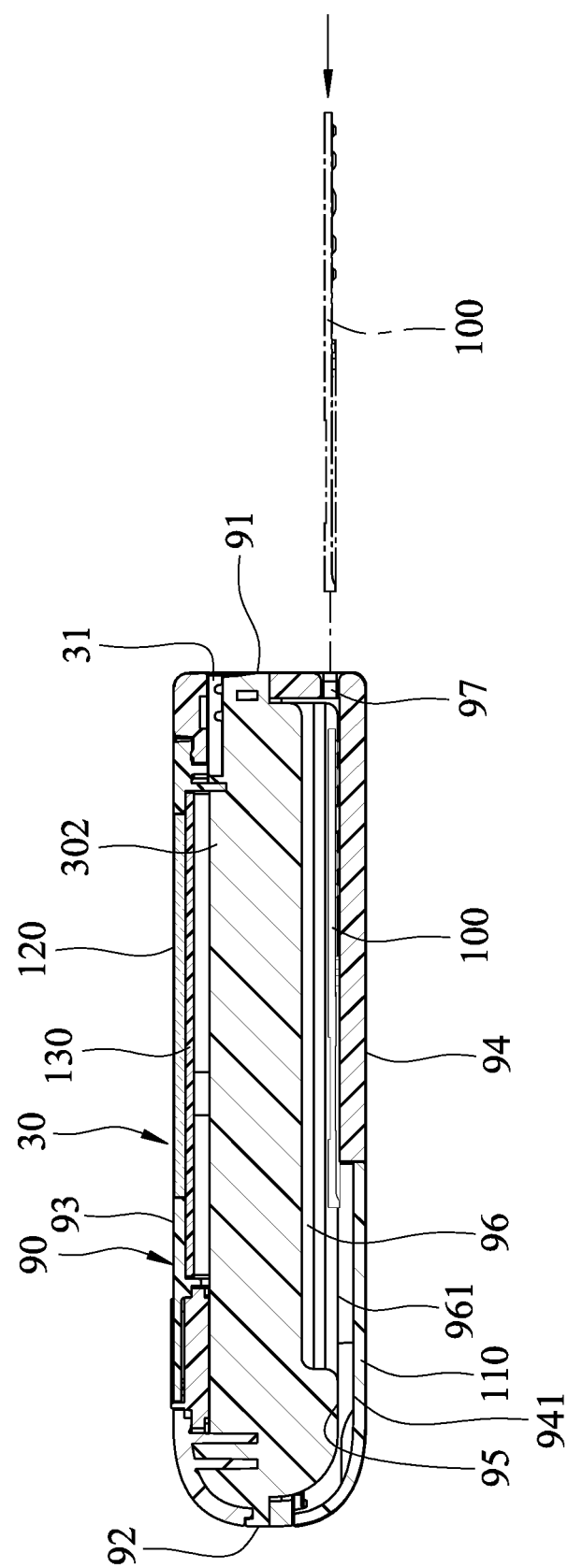
FIG. 18 is a sectional view of the fourth preferred embodiment, illustrating how a used biosensor strip is inserted into the waste storage compartment via an insertion hole.
Figure 19:
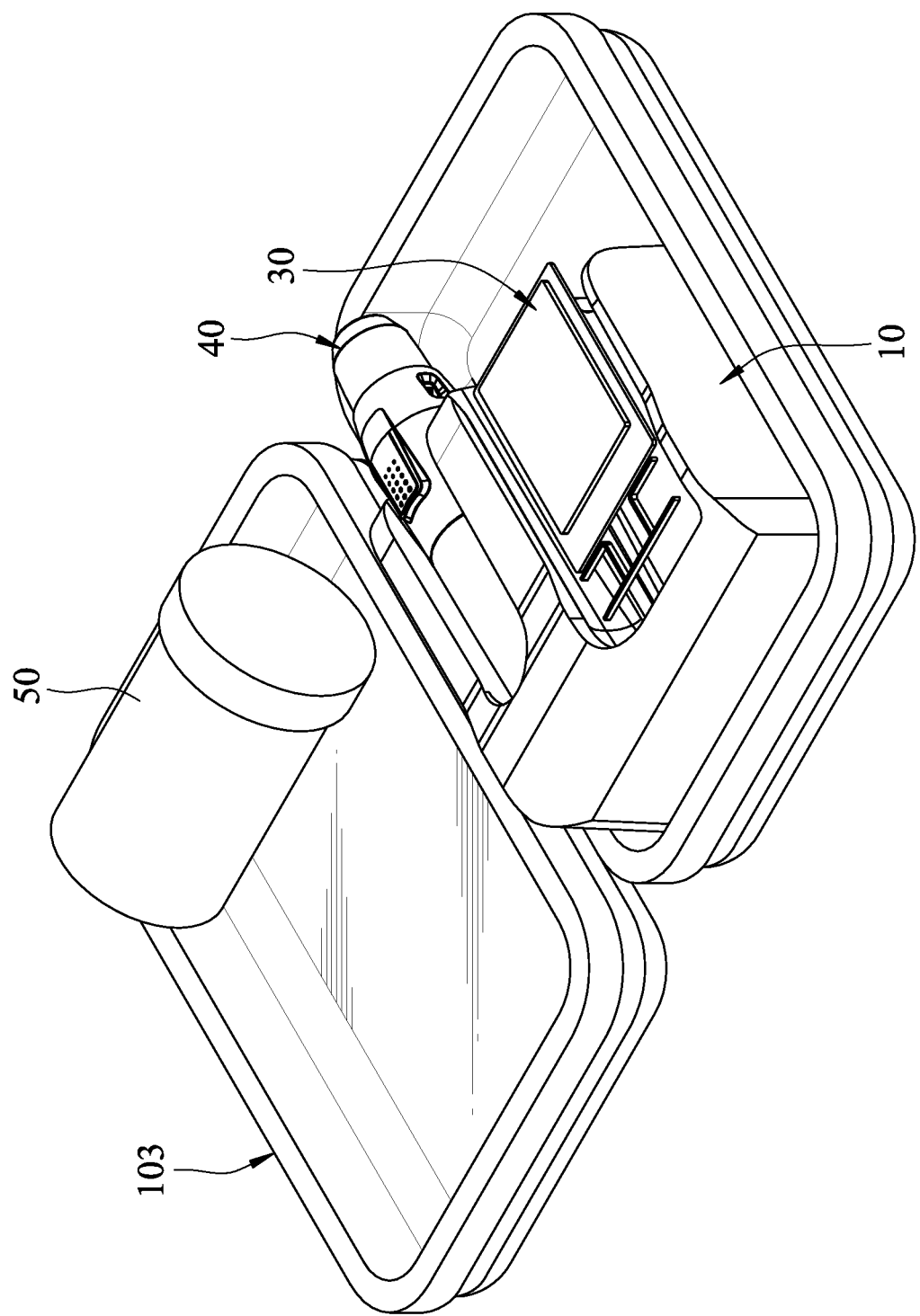
FIG. 19 is a perspective view of a biological testing device according to the fifth preferred embodiment of this invention being disposed in a storage box.
Figure 20:
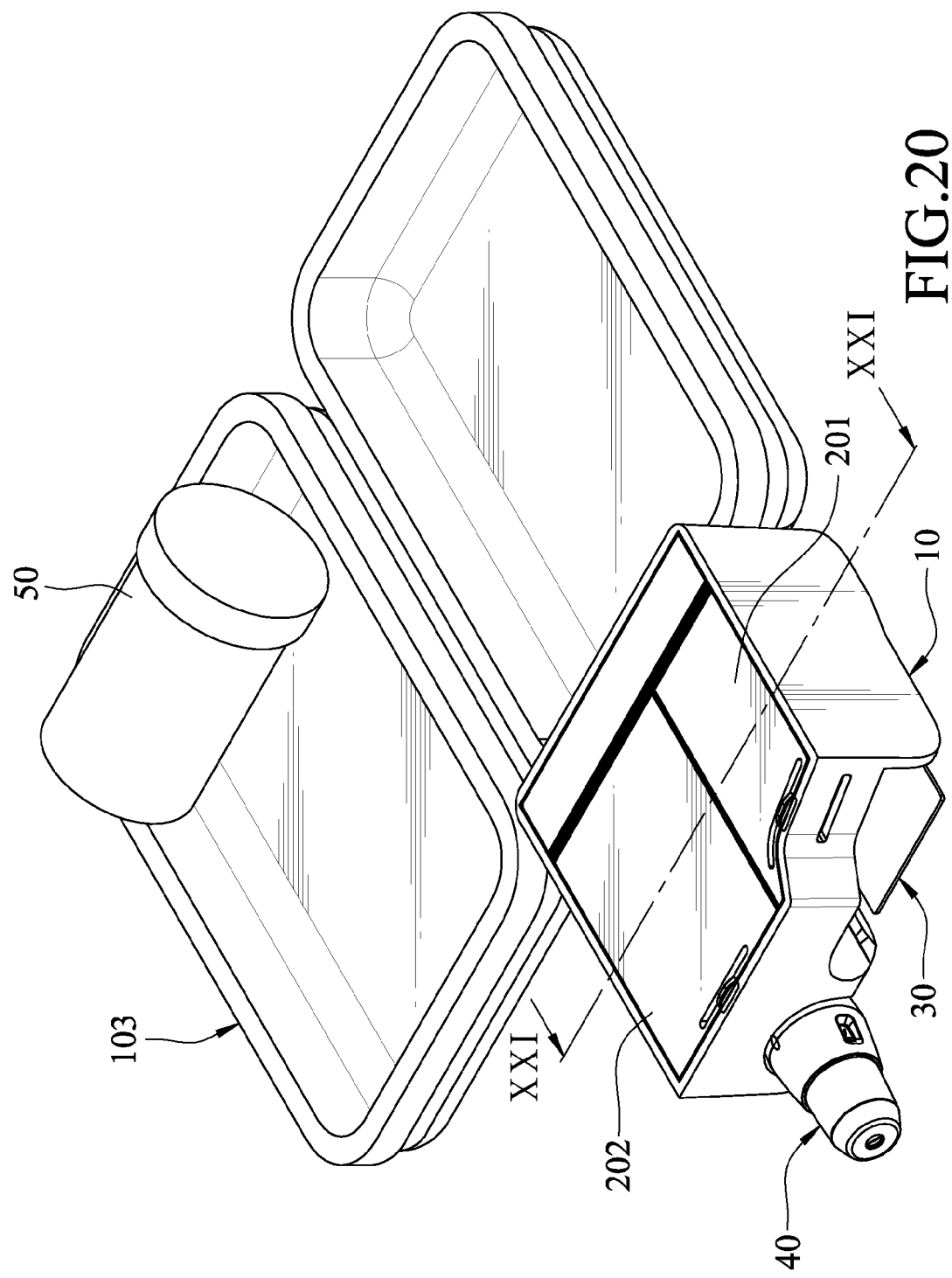
FIG. 20 is a view similar to FIG. 19, but with the biological testing device being moved out of the storage box.
Figure 21:
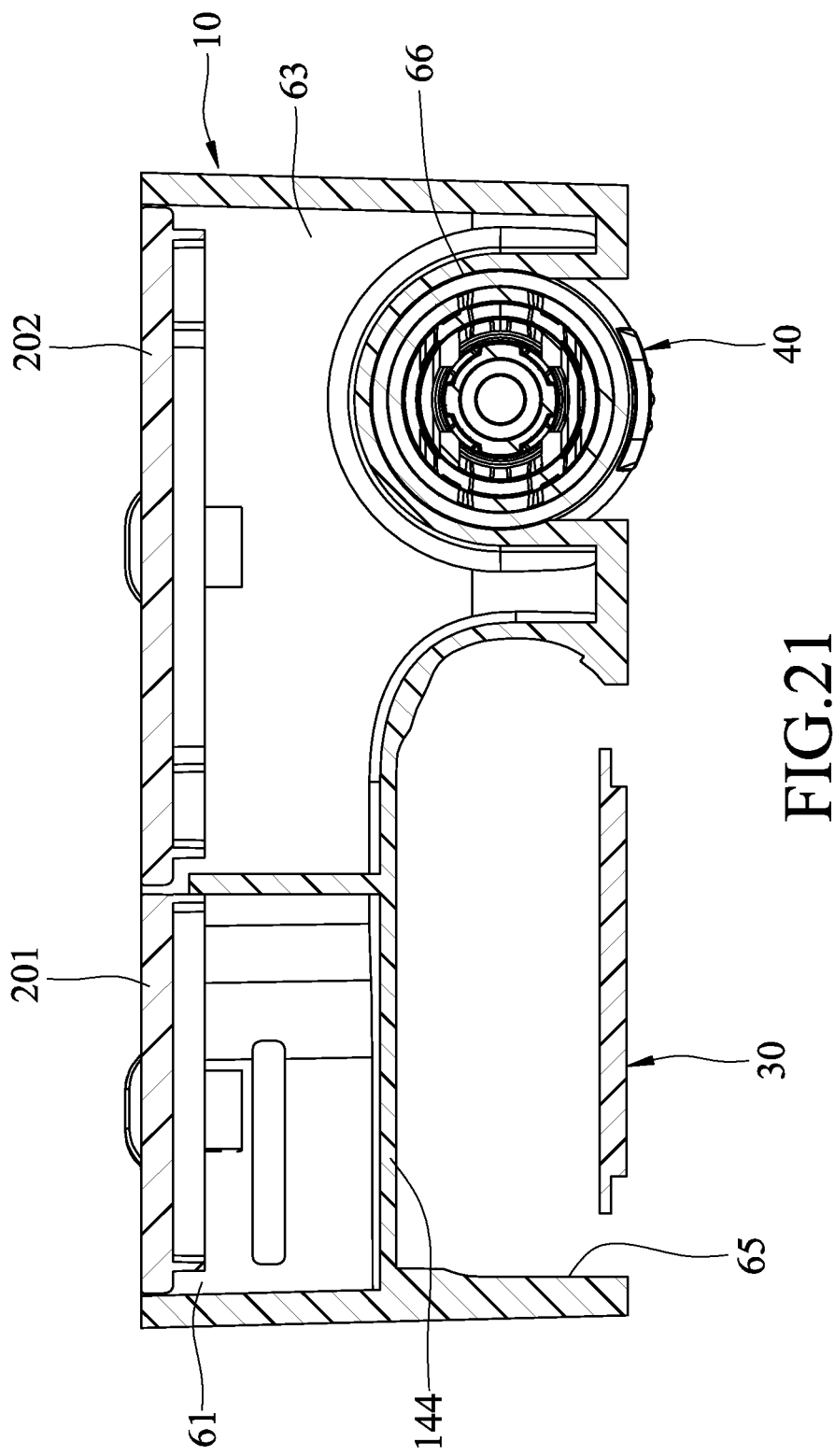
FIG. 21 is a sectional view of the fifth preferred embodiment taken along line XXI-XXI of FIG. 20.
Figure 22:
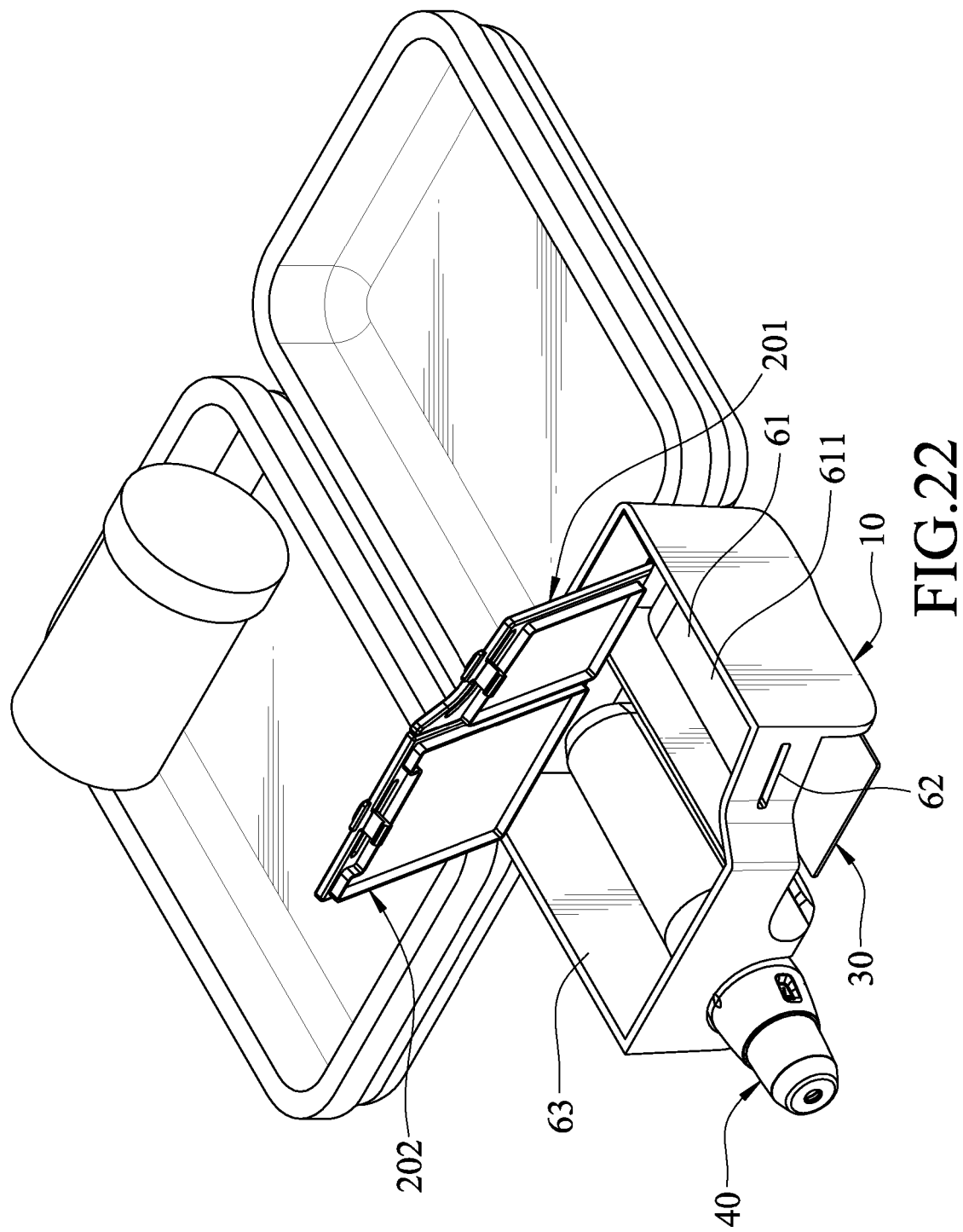
FIG. 22 is a view similar to FIG. 20, but with first and second covers in an open position.

Referring to FIGS. 16 to 18, the fourth preferred embodiment of the biological testing device according to the present invention is shown to be similar to the first preferred embodiment. Particularly, the housing body 90 of the biological testing device has a front end 91, a rear end 92, a top surface 93, a bottom surface 94, a meter storage compartment 95 receiving the testing meter 30, a waste storage compartment 96 having a waste take-out opening 961 formed in an indented portion 941 of the bottom surface 94 which is proximate to the rear end 92, and an insertion hole 97 formed in the front end 91 below the insertion groove 31 and communicated with the waste storage compartment 96. The housing body 90 may also be provided with a spare compartment (not shown) at an appropriate position.

However, in this embodiment, the meter casing of the testing meter 30 is also the housing body 90 of the biological testing device. The testing meter 30 is preferably a blood glucose meter, and includes a display screen 120 exposed from the top surface 93, and a processor 130 disposed below and electrically connected to the display screen 120. A bottom cover 110 is detachably disposed on the indented portion 941 of the bottom surface 94 to openably close the waste take-out opening 961.

After testing, the biosensor strip 100 is pulled and removed from the housing body 90, and is inserted into the insertion hole 97 so as to be received in the waste storage compartment 96 for temporary storage. At this time, the waste take-out opening 961 is covered by the bottom cover 110 to ensure safe storage of the used biosensor strip 100 in the waste storage compartment 96. It is understandable that when the bottom cover 110 is detached from the housing body 90, the used biosensor strip 100 can be removed from the waste storage compartment 96 for discard.

The advantages described in the first preferred embodiment can be similarly achieved using the fourth preferred embodiment.

Referring to FIGS. 19 to 22, the fifth preferred embodiment of the biological testing device according to the present invention is shown to be similar to the first preferred embodiment. In particular, the biological testing device comprises a housing body 10, a testing meter 30, a lancing pen 40 and a biosensor strip container 50. However, in this embodiment, a storage box 103 is provided for housing the biological testing device. Further, a first cover 201 is pivoted to the housing body 10 to openably close the waste storage compartment 61, and a second cover 202 is pivoted to the housing body 10 to openably close the spare compartment 63. Spare lancets (not shown) may be similarly stored in the spare compartment 63.

After testing, the biosensor strip (see FIG. 3) is inserted into the insertion hole 62 so as to be received in the waste storage compartment 61 for temporary storage. At this time, the waste take-out opening 611 is covered by the first cover 201 to ensure safe storage of the used biosensor strip in the waste storage compartment 61. It is understandable that the used biosensor strip can be removed from the waste storage compartment 61 via the waste take-out opening 611 for discard when the first cover 201 is open.

The advantages described in the first preferred embodiment can be similarly achieved using the fifth preferred embodiment.

In summary, the biological testing device of this invention not only can facilitate easy and quick testing operation, but also can facilitate temporary safe storage of the used biosensor strip. Hence, the object of the present invention can be realized.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A biological testing device for testing a sample, comprising:
   a housing body having a meter storage compartment, a front end, a rear end, a top surface, and a bottom surface;
   a lancing pen;
   a testing meter that is disposed in said meter storage compartment and that operates with a biosensor strip which is disposed after being used; and
   a cover;
   wherein said housing body further has
      a waste storage compartment that is separated from said meter storage compartment and that has a waste take-out opening formed in said bottom surface,
      a pen storage compartment adjacent to said meter storage compartment for receiving said lancing pen,
      a spare compartment having a spare take-out opening that is formed in said bottom surface, and
      an insertion hole formed in said front end and communicated with said waste storage compartment for inserting the used biosensor strip into said waste storage compartment;
   wherein said waste take-out opening is larger than said insertion hole, said insertion hole being separated from said waste take-out opening and having a narrow oblong shape substantially similar to a cross section of the used biosensor strip, said waste take-out opening being normally closed and being openable for permitting taking out of the used biosensor strip from said waste storage compartment; and
   wherein said cover has
      a positioning section positioned on said bottom surface,
      a first cover section that extends rearwardly from said positioning section, that is pivotable relative to said positioning section, and that openably closes said waste and spare take-out openings,
      a second cover section that is positioned on said top surface, that is pivotable relative to said positioning section, and that openably covers said testing meter and said lancing pen,
      a first pivot section that extends forwardly from said positioning section, and that is pivotable relative to said positioning section, and
      a second pivot section that extends upwardly from said first pivot section, that is pivotable relative to said first pivot section, and that openably covers said insertion hole, a front end of said testing meter, and a front end of said lancing pen, wherein said second cover section extends rearwardly from said second pivot section.

2. The biological testing device of claim 1, wherein said bottom surface has a non-indented portion proximate to said rear end, an indented portion proximate to said front end, and a shoulder formed between said non-indented portion and said indented portion, said waste and spare take-out openings being formed in said indented portion, said housing body further having an operating groove formed in said non-indented portion and having a front end extending through said shoulder into said indented portion, said positioning section being positioned on said indented portion, said first cover section being positioned on said indented portion and further openably closing a portion of said operating groove.

3. The biological testing device of claim 1, wherein said housing body further has a separation wall that separates said meter storage compartment and said waste storage compartment and that is spaced apart from said insertion hole by a first distance, an inner side of said first cover section being spaced apart from said insertion hole by a second distance.

4. The biological testing device of claim 1, further comprising a biosensor strip container, said housing body further having a side surface, and a container storage compartment that is formed in proximity to said rear end and that opens at said side surface for receiving said biosensor strip container.

5. The biological testing device of claim 1, wherein said testing meter has a display screen exposed from said top surface of said housing body, and a processor disposed below and connected electrically to said display screen.

6. The biological testing device of claim 1, wherein said biological testing device is a blood glucose meter.

* * * * *